United States Patent [19]

Ichikawa et al.

[11] Patent Number: 4,844,905
[45] Date of Patent: Jul. 4, 1989

[54] GRANULE REMAINING IN STOMACH

[75] Inventors: Masaki Ichikawa, Kakamihara; Sumio Watanabe, Aichi; Yasuo Miyake, Inuyama, all of Japan

[73] Assignee: Eisai Co., Ltd., Tokyo, Japan

[21] Appl. No.: 13,832

[22] Filed: Feb. 12, 1987

[30] Foreign Application Priority Data

Feb. 24, 1986 [JP] Japan .................................. 61-37450

[51] Int. Cl.⁴ .......................... A61K 9/48; A61K 9/16
[52] U.S. Cl. .................................... 424/451; 424/452; 424/466; 424/494; 424/497
[58] Field of Search ............... 424/468, 472, 474, 475, 424/480, 482, 494, 495, 497, 499, 501, 502, 451, 452, 466; 427/3

[56] References Cited

U.S. PATENT DOCUMENTS

| | | | |
|---|---|---|---|
| 3,667,929 | 6/1972 | Fleming | 71/67 |
| 4,101,650 | 7/1978 | Umezawa | 424/44 |
| 4,172,120 | 10/1979 | Todd et al. | 424/501 X |
| 4,359,483 | 11/1982 | Kaetsu et al. | 427/3 X |
| 4,533,562 | 8/1985 | Ikegami et al. | 427/3 |
| 4,600,645 | 7/1986 | Ghebre-Sellassie et al. | 427/3 X |

FOREIGN PATENT DOCUMENTS 900824 2/1985 Belgium .
2468/1983 8/1984 Ireland .

OTHER PUBLICATIONS

Conception and in vivo investigation of peroral sustained release floating dosage forms with enhanced gastrointestinal transit, H. M. Ingami, et al.
Chemical Abstracts, vol. 106, No. 18, May 4,1987, p. 364, and Int'l Journal of Pharmaceutics, 35, (1987), pp. 157–164.

Primary Examiner—Michael Lusignan
Attorney, Agent, or Firm—Flynn, Thiel, Boutell & Tanis

[57] ABSTRACT

A granule of drug to remain in the stomach comprises a core comprising a pharmaceutically effective ingredient, a foaming layer coated on said core and an expansive film coated on said layer.

10 Claims, 3 Drawing Sheets

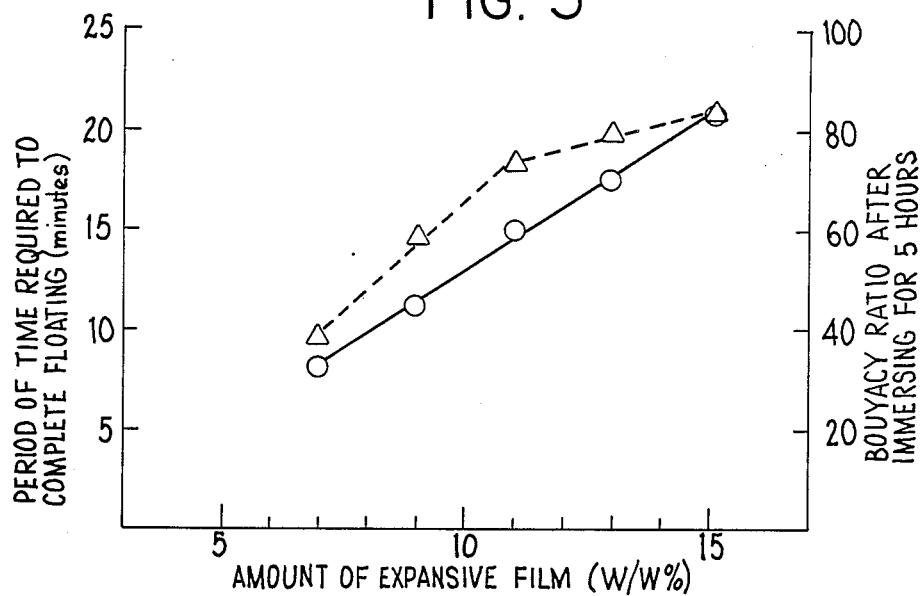
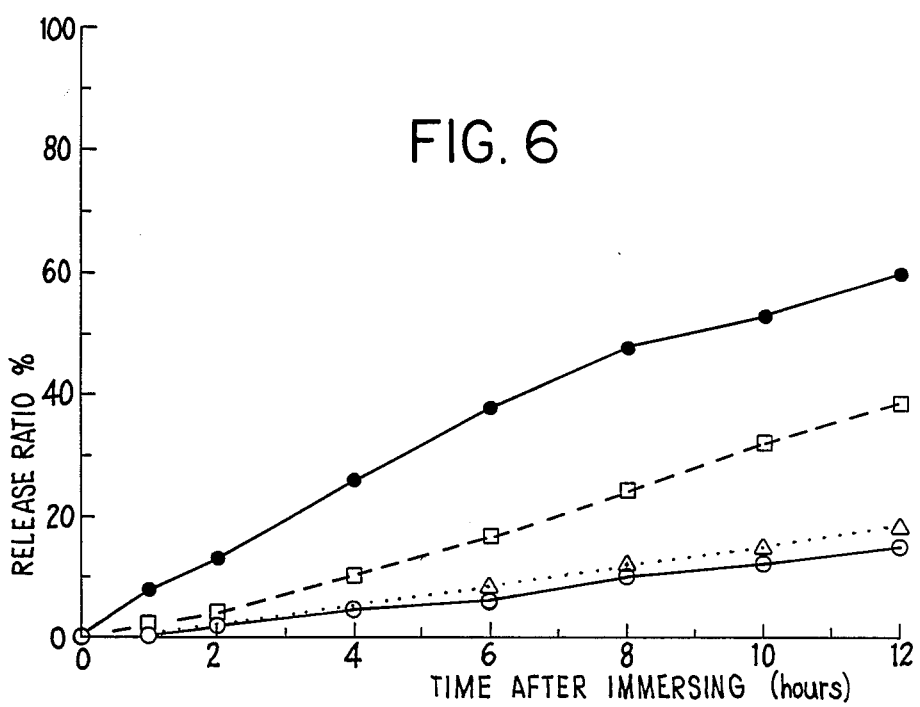

GRANULE REMAINING IN STOMACH

This invention relates to a granule remaining in the stomach. More particularly, it relates to a granule which is particularly designed to remain in the stomach for a prolonged period of time when orally administered in the form of a therapeutic or diagnostic preparation to thereby enhance the effect of each ingredient contained therein. Accordingly the present invention is utilized mainly in the field of pharmaceuticals.

PRIOR ART

Generally a water-soluble preparation which is orally administered remains in the stomach for only one or two hours before it is transported into the duodenum, so that absorption of the ingredients contained therein terminates in a relatively short period. Even in the case of a sustained release preparation wherein the releasing rates of the ingredients contained therein are controlled, the effects would last for eight to ten hours at the longest. It has been already known that these circumstances bring about the device of a preparation remaining in the stomach which is designed to exhibit sufficiently persistent effects, free from the limitations as discussed above, when taken once a day.

U.S. Pat. No. 3,976,764, which corresponds to Japanese Patent Publication No. 12411/1980, has disclosed a preparation remaining in the stomach for the first time. This preparation has a solid hollow structure or is filled with a foam material, which makes it floatable in the gastric juice. Subsequently U.S. Pat. No. 4,055,178 has provided a drug delivery device which allows a drug contained therein to float on the gastric juice while preventing it from being turned upside down. Recently U.S. Pat. Nos. 4,126,672, 4,140,755, 4,167,558 and 4,424,235 have disclosed preparations remaining in the stomach each based on a hydrodynamically balanced system (HBS). Namely, a drug is mixed with hydrocolloid(s), which are polymers capable of forming a gel, and formulated into a capsule or a tablet. Thus the capsule or tablet would swell and set to gel upon contact with gastric juice while maintaining its original shape, thus being able to float in the gastric juice as long as five or six hours. Thus the active ingredient contained therein can be gradually released through the gel layer and absorbed in the intestinal tact for a prolonged period of time, which makes it possible to maintain a constant level thereof in the blood. Examples of the active ingredient are acetysalicylic acid, antacid compounds, benzodiazepine and L-dopa. Examples of the hydrocolloids are methylcellulose, hydroxypropylcellulose, hydroxypropylmethylcellulose, hydroxyethylcellulose, and sodium carboxymethylcellulose. Further U.S. Pat. No. 4,434,153 has recently disclosed a drug delivery system comprising a hydrogel matrix containing a plurality of tiny pills each comprising a core coated with a fatty acid and wax. In this system, the absorption of the active ingredient is controlled through the residence thereof in the stomach and the sustained release thereof in the intestine.

PROBLEM TO BE SOLVED BY THE INVENTION

As shown above, most conventionally devised preparations remaining in the stomach are in the form of tablets or capsules. Thus a single unit capable of remaining in the stomach is relatively large. However it is possible that such a large preparation might migrate into the duodenum as a whole immediately after the administration and thereby fail to exhibit any effect in the stomach or, contrary to this, remain in the stomach too long, when the behavior of the preparation is affected by, for example, the amount, pH value or viscosity of the content of the stomach. In order to avoid these troubles, it is required to formulate such a preparation into smaller units each capable of remaining in the stomach for a long time. That is to say, it is urgently required to develop granules remaining in the stomach.

Under these circumstances, the present invention aims at providing a granule remaining in the stomach and establishing a technique for producing said granule. More particularly, the present invention intends to develop granules which can float on the gastric juice rapidly after administration and maintain this buoyant condition for a prolonged period of time.

After the extensive studies for attaining the above object, we have found that the abovementioned problem can be solved by coating a core with a foam layer and an expansive film in this order, thus completing the present invention. Accordingly, the gist of the present invention is to provide a granule remaining in the stomach, characterized in that a core is coated with a foam layer and an expansive film in this order.

The invention provides a granule of drug to remain in the stomach, which comprises a core comprising a pharmaceutically effective ingredient, a foaming layer coated on said core and an expansive film coated on said layer.

It is preferable that said foaming layer comprises a bicarbonate or a combination of a bicarbonate and an organic acid. The foaming layer more preferably comprises an inner layer comprising a bicarbonate and another outer layer comprising an organic acid.

It is preferable that the expansive film comprises a polymer to allow the gastric juice to pass therethrough and expand by foam produced by the action between the gastric juice and the foaming layer.

Now the present invention will be described in more detail.

By the core is meant a nucleus to be located at the center of the granule of the present invention. A spherical granule containing a drug may be used as the core. Alternately a so-called seed coated with a layer containing a drug may be employed. Further a core may be employed as such. The core may be coated with a so-called barrier layer, if required. The barrier layer may comprise a mixture of, for example, stearic acid, talc, ethylcellulose and shellac. The mixture may be suspended in, for example, aqueous ethanol and employed for coating. In order to facilitate and secure the coating operation of the core with the foam layer, it is often preferable that the surface of the core consists of a barrier layer. The core preferably has a spherical form. Thus it is desirable to use a granule which has been made spherical in an appropriate manner as a seed for producing the core.

By the foam layer is meant a layer which evolves a gas, thus foaming upon contact with the gastric juice. An example of the gas is carbon dioxide. In this case, the above object can be achieved by introducing a bicarbonate optionally combined with an organic acid into the foaming layer. Usually sodium bicarbonate is used as the bicarbonate while examples of the organic acid are tartaric, succinic and citric acids. When a combination of a bicarbonate and an organic acid is employed, it is preferable that each component forms a layer independently. Namely, the foam layer preferably has a double-layer structure comprising a bicarbonate layer and an organic acid layer. In this case, the order of these layers is not strictly limited. However it is preferable that the bicarbonate forms an internal layer while the organic acid forms an external one from the viewpoint of the order in which they are brought into contact with the acidic components of the gastric juice. Besides the bicarbonate or the organic acid, each layer may further contain excipients appropriately selected from among, for example, talc, light silicic anhydride, calcium stearate and hydroxypropylcellulose to thereby facilitate the coating operation. It is recommended that the amount of the foam layer is 5 to 20% by weight, preferably 10 to 15% by weight, of the core, although the present invention is not restricted thereby. Upon coating, the components of the foam layer are dissolved and/or suspended in 85 to 100% aqueous ethanol and the obtained suspension is applied around the core with, for example, a fluid granulator followed by drying.

By the expansive film is meant a film which can allow the gastric juice to penetrate into the inside of the granule when the granule of the invention is in contact with the gastric juice; and then expand like a balloon because of the gas evolved within the granule to thereby retain the gas within the granule for a required period of time. It is not particularly difficult for usual polymeric films to exert these functions. Thus, appropriate polymers such as polyvinyl acetate, acrylic resins, shellac, hydroxypropylmethylcellulose phthalate, cellulose acetate phthalate, methylcellulose, ethylcellulose or hydroxypropylmethylcellulose may be used as the film. Alternately, a composition comprising some of these polymers at an appropriate ratio may be employed. In order to facilitate and secure the coating of the film, the film may further contain a plasticizer such as monoglyceride, or calcium stearate in small amounts. These procedures may be appropriately effected in a conventional manner employed in the art for coating a solid material with a polymer film. Thus the components of the film may be dissolved in 60 to 90% aqueous ethanol and then the subject may be coated with the obtained solution in a fluidized bed coating device followed by drying. The subject to be coated with the expansive film is the core which has been previously coated with the foam layer. Namely, the core is coated with the foam layer and then with the expansive film. It is usually recommended that the amount of the expansive film is 5 to 20% by weight, preferably 7 to 15% by weight, of the core. However the ratio may be appropriately controlled depending on the components of the film and the present invention is not restricted thereby.

The granule of the present invention is available in therapeutic and diagnosic preparations required to remain in the stomach for a prolonged period of time. Thus it can be widely applied to, for example, analgesics such as dextromethorphan hydrobromide; antipasmodics such as scopolamine hydrobromide; local anesthetics such as trocine; digestants such as pepsin; antitussives such as ephedrine; antiallergics such as diphedrine; cardiac diuretics such as aminophylline; and contrast media such as barium sulfate. These drugs may be usually contained in the core of the granule of the present invention. However it may be sometimes blended into the expansive film. For example, the expansive film may contain a small amount of a contrast medium or a local anesthetic.

The granules of the present invention may be orally administered as such. Alternately they may be filled in a capsule or formulated into a tablet together with appropriate excipient(s) and orally administered. All of these preparations contain the granules of the present invention.

BRIEF DESCRIPTION OF THE DRAWINGS

FIG. 5 corresponds to FIG. 5 as described in Example 4 and is a graph showing the relationship between the period required for the completion of the floating and the buoyancy ratio after immersing the sample in the buffer solution for five hours and the weight of the expansive film.

FIG. 6 corresponds to FIG. 6 as described in Example 5 and is a graph showing the release ratio and the period of immersing the sample in the buffer solution.

Figure 1:
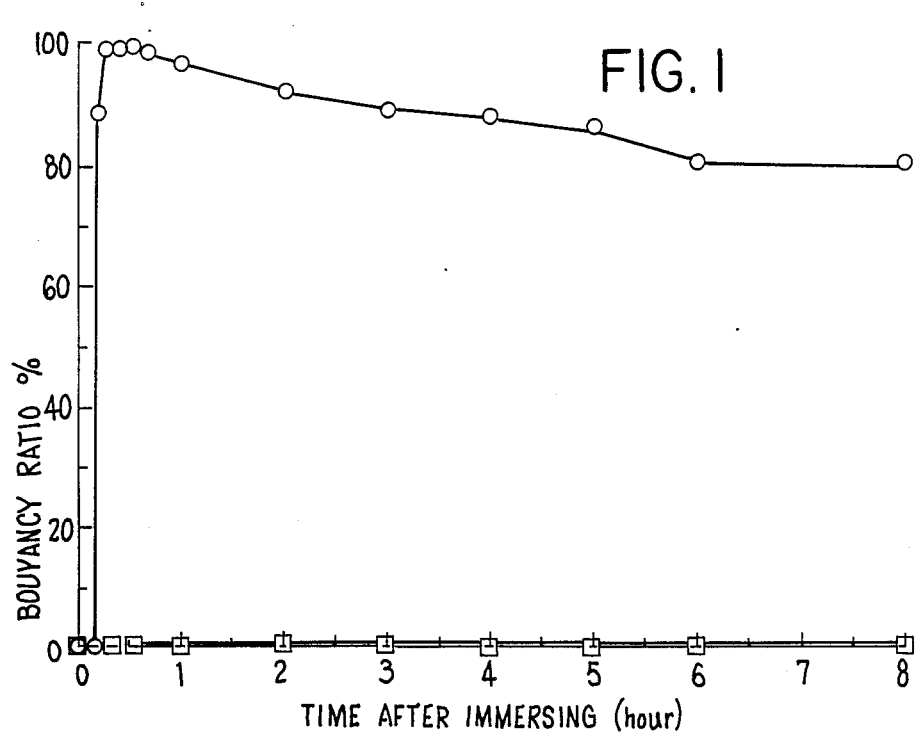
FIG. 1 corresponds to FIG. 1 as described in Example 1 and is a graph showing the relationship between the buoyancy ratio and the period of immersing the sample in the buffer solution.

The highest effect of the present invention can be achieved by orally administering a preparation which integrally contains various granules differing from each other in their residence times in the stomach. In this case, some granules would rapidly reach the intestinal tract, which makes early absorption of active ingredient(s) possible. On the other hand, other granules would slowly reach the intestinal tract, which makes later absorption thereof possible. As a result, an immediate effect and a sustained effect can be simultaneously achieved by a single administration. Thus the embodiment of the present invention further includes an integral preparation containing various types of granules of the present invention differing from each other in the residence time in the stomach, and optionally, are used together with conventional granules that do not remain in the stomach and have a foam layer.

The expression "remaining in the stomach" is generally interpreted as follows. A pharmaceutical preparation orally administered would remain in the stomach usually for one to two hours in average, although it varies depending on the subject, the health condition thereof, food taken by the subject, day or night and the mental condition of the subject. Thus a preparation designed to remain in the stomach exceeding the usual period, for example, two hours is considered to belong to the abovementioned type. However this definition is only an idealized concept and it is required to establish a more concrete one defined by the particular characteristics or behaviors of preparations. Therefore, a preparation remaining in the stomach is defined in the present invention as one whose behavior characteristics suggest that it is floatable in gastric juice. The behavior characteristics as described above are determined from the time required for floating all granules immersed in an artificial gastric juice, for example, an acetate buffer solution (pH 4), i.e., the period required for the completion of the float, and the proportion of buoyant granules which do not yet settle when a predetermined period of time has elapsed after immersing the granules in water, i.e., the buoyancy ratio.

EFFECT OF THE INVENTION

When immersed in the artificial gastric juice, granules which are not particularly designed to remain in the stomach would settle without floating. Thus none of these granules are observed buoyant on the surface of the artificial gastric juice. In this case, the period required for the completion of the float is infinitely long and the buoyancy ratio after, for example, five hours is 0%. On the other hand, when the granules of the present invention are immersed in the artificial gastric juice, foaming occurs within each granule, which allows it to come up to the surface of the artificial gastric juice. In addition, a number of the granules remains buoyant without settling after a predetermined period of time. In this case, the time required for the completion of the floating is very short, for example, 15 minutes, while the buoyancy ratio after immersing in the fluid for five hours is as high as, for example, 75%. These behavior characteristics suggest that the granules of the present invention are floatable in the artificial gastric juice. Thus they can be defined as granules remaining in the stomach.

As obviously described above, the present invention exhibits an effect of allowing granules to remain in the stomach to thereby give various sustained effects, in particular, pharmaceutical ones.

EMBODIMENTS OF THE INVENTION

To further illustrate the present invention, the following Examples will be given.

EXAMPLE 1

1112 g of spherical granules of white sugar corn starch, approximately 1 mm in diameter, were introduced into a centrifugal fluid granulator. A suspension obtained by previously dissolving and/or suspending 150 g of calcium stearate, 50 g of talc, 10 g of ethylcellulose and 10 g of shellac in ethanol was added thereto to thereby give cores each coated with a barrier layer. Then a suspension obtained by previously dissolving and/or suspending 172 g of ground sodium bicarbonate, 172 g of talc, 46 g of light silicic anhydride and 12 g of hydroxypropylcellulose in 95% aqueous ethanol was added to the cores to thereby coat each core with a bicarbonate layer. Subsequently, a suspension obtained by previously dissolving and/or suspending 190 g of ground tartaric acid, 106 g of talc, 38 g of light silicic anhydride and 130 g of calcium stearate in absolute ethanol was added thereto to thereby further coat each core with a tartaric acid layer. Finally, 300 g of the obtained granules, each having a foam coating layer, were introduced into a fluidized bed coating device and a solution obtained by previously dissolving a film material comprising 26.1% of vinyl acetate, 36.5% of shellac, 31.3% of hydroxypropylmethylcellulose phthalate, 5.2% of acetyl monoglyceride and 0.9% of calcium stearate in 80% aqueous ethanol was added thereto to thereby coat each granule with an expansive film. After drying, the granules of the present invention were obtained. In the granule of the present invention, the amount of the sodium bicarbonate was 13% by weight of the core while the amount of the expansive film was 11% by weight of the core coated with the foam layer.

EXAMPLE 2

800 g of spherical granules of white sugar corn starch were introduced into a centrifugal fluid granulator and a suspension obtained by previously dissolving and/or suspending 200 g of ground barium sulfate, 35 g of talc, 35 g of light silicic anhydride and 22 g of hydroxypropylcellulose in 95% methanol was added thereto to thereby coat the former with the latter. Employing each granule thus coated as a core, the procedure of Example 1 was followed to thereby coat the core with a barrier layer, a bicarbonate layer and an expansive film layer in this order. After drying, the granules of the present invention were obtained. The period required for the completion of floating of these granules was 10 to 14 minutes while the buoyancy ratio thereof after immersing the same in the artificial gastric juice was 82%. The specific gravity of the granules before the immersing was 1.45 while that thereafter was 0.54. Each specific gravity showed little variation.

EXAMPLE 3

The procedure of Example 1 was followed except that the spherical granules of white sugar corn starch were replaced with spherical sustained release granules containing 20% of dextromethorphan hydrobromide to thereby give the granules of the present invention.

EXAMPLE 4

3-g portions of the granules of the present invention as produced in Example 2 were packed into hard capsules to give capsules according to the present invention.

EXAMPLE 5

300-g portions of the granules of the present invention as produced in Example 2 were packed into hard capsules to give capsules according to the present invention.

EFFECTS OF THE INVENTION

In order to illustrate the effects of the present invention, the following Experimental Examples will be given.

Experimental Example 1

Sample:

The granules of the present invention as produced in Example 1 were used as a sample. Separately a control sample was prepared in the following manner. 1112 g of spherical granules of white sugar corn starch, approximately 1 mm in diameter, were introduced into a centrifugal fluid granulator and a suspension obtained by previously dissolving and/or suspending 740 g of calcium stearate, 248 g of talc, 49 g of ethylcellulose and 49 g of shellac in absolute ethanol was added thereto to thereby coat each granule with a barrier layer comprising the suspension. Thus cores were obtained. 300 g of the obtained cores were introduced into a fluidized bed coating device and a solution obtained by previously dissolving a film material comprising 26.1% of vinyl acetate, 36.5% of shellac, 31.3% of hydroxypropylmethylcellulose phthalate, 5.2% of acetyl monoglyceride and 0.9% of calcium stearate in 80% aqueous ethanol was added thereto. Thus each core was coated with an expansive film. The amount of the expansive film was adjusted to 11% by weight of the core. The granules thus obtained were employed as a control sample. Each granule of the test sample had the same weight as that of the control sample, although the former had the foam layer while the latter was lacking in the same.

Method:

Each sample was immersed in an acetate buffer solution (pH 4.0) and the buoyancy ratio thereof was determined with the lapse of time under shaking the same at a rate of 80 times per minutes. The buoyancy ratio was expressed in the ratio of buoyant granules to the total granules immersed in the buffer solution. This operation was effected thrice for the test sample and once for the control sample.

Result:

FIG. 1 shows the result, wherein —O—O— represents the data (average values) of the test sample, white —□—□— represents that of the control sample. Table 1 shows the buoyancy ratio of each sample after immersing in the buffer solution for five hours obtained from FIG. 1.

TABLE 1

|  | Test sample | Control sample |
|---|---|---|
| Period required for the completion of floating | 14 to 15 min | not floating |
| Buoyancy ratio after immersing in buffer for 5 hours | 75% | 0% |

FIG. 1 and Table 1 suggest that the granules of the present invention are floatable because of the presence of the foam layer and, consequently, remain in the stomach.

Experimental Example 2

Sample and Method:

The procedure of Example 1 was followed except that the amount of the sodium bicarbonate of the granules of the present invention as produced in Example 1 was adjusted to 10%, 12%, 13% and 14.5% on a weight basis of the cores to thereby give four samples. The buoyancy ratio of each sample was determined in the same manner as the one described in Experimental Example 1. From the result thus obtained, the period required for the completion of floating of the sample and the buoyancy ratio after immersing the same in the buffer solution for five hours were determined.

Figure 2:
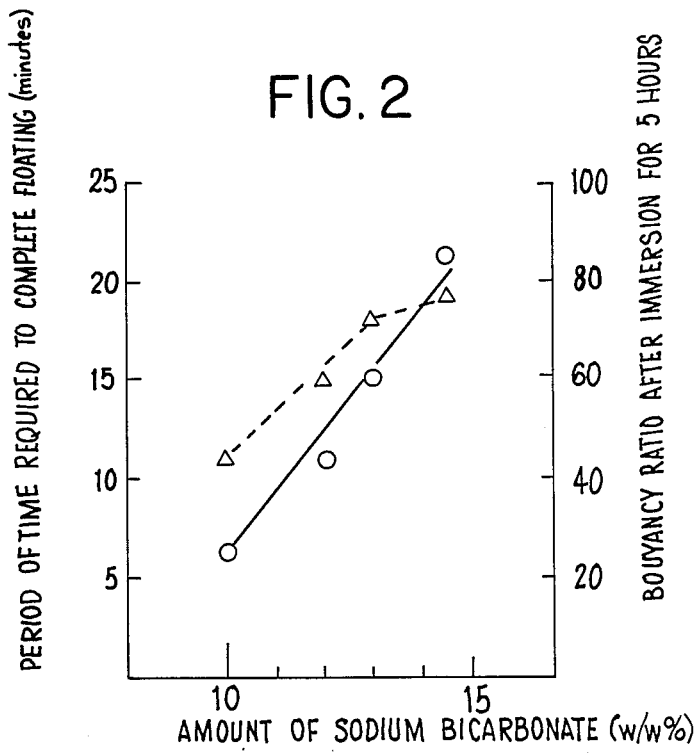
FIG. 2 corresponds to FIG. 2 as described in Example 2 and is a graph showing the relationship between the period required for the completion of the floating and the buoyancy ratio after immersing the sample in the buffer solution for five hours.

Result:

FIG. 2 shows the result, wherein —O—O— represents the data of the period required for the completion of the floating, while —Δ—Δ— represents that of the buoyancy ratio after immersing in the buffer solution for five hours. FIG. 2 suggests that the floatability of the granules of the present invention increases with an increase in the weight of the sodium bicarbonate to allow the granules to remain in the stomach for a longer period of time.

Experimental Example 3

Sample and Method:

The granules of the present invention as produced in Example 1 were used as a sample. The buoyancy ratio was determined with the lapse of time in the same manner as the one described in Experimental Example 1 except that the pH value of the acetate buffer solution was adjusted to 1.0 to 5.0. Further, the buoyancy ratio was determined in the same manner as described therein except that the pH value of the acetate buffer solution was adjusted to 3.0 and that the viscosity of the solution was controlled by adding hydroxymethylpropylcellulose.

Figure 3:
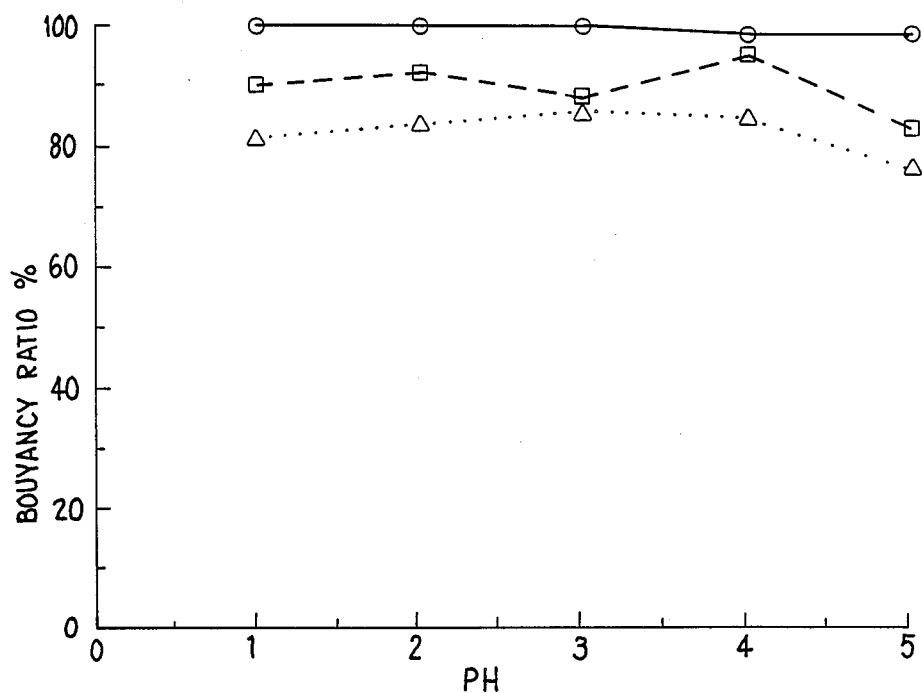
FIG. 3 corresponds to FIG. 3 as described in Example 3 and is a graph showing the relationship between the buoyancy ratio and pH value.
Figure 4:
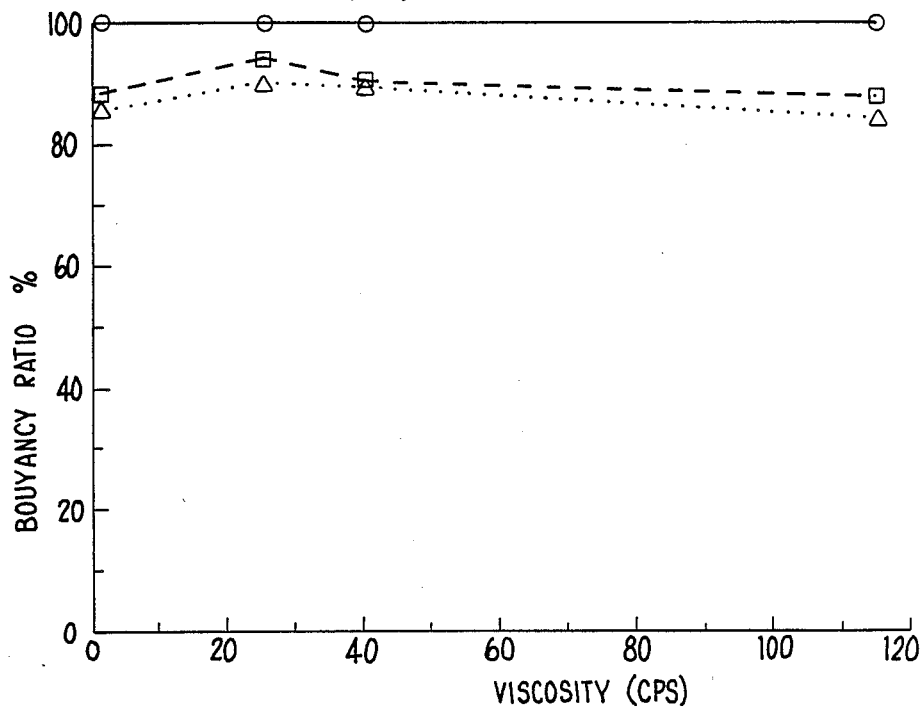
FIG. 4 corresponds to FIG. 4 as described in Example 3 and is a graph showing the relationship between the buoyancy ratio and viscosity.

Results:

FIGS. 3 and 4 show the results. FIG. 3 is a graph showing the relationship between the pH value of the acetate buffer solution and the buoyancy ratio, while FIG. 4 is a graph showing the relationship between the viscosity of the acetate buffer solution (pH 3.0) and the buoyancy ratio. In each FIG., —O—O—, —□—□— and —Δ—Δ— represent the data obtained after immersing the sample in the acetate buffer solution for 15 minutes, for two hours and for four hours, respectively. FIGS. 3 and 4 suggest that the ability of remaining in the stomach of the granules of the present invention is not affected by the pH value or the viscosity.

Experimental Example 4

Sample and Method:

The procedure of Experimental Example 1 was followed except that the amount of the expansive film of the granules of the present invention as produced in Example 1 was adjusted to 7%, 9%, 11%, 13% and 15% on a weight basis of the cores coated with the foam layer to thereby give five samples. The buoyancy ratio of each sample was determined with the lapse of time in the same manner as described in Experimental Example 1. From the result thus obtained, the period required for the completion of floating of the sample and the buoyancy ratio after immersing the same in the buffer solution for five hours were determined.

Result:

FIG. 5 shows the result, wherein —O—O— represents the data of the period required for the completion of the floating, while —Δ—Δ— represents that of the buoyancy ratio after immersing the sample in the buffer solution for five hours. FIG. 5 suggests that the period required for the completion of the floating is increased with an increase in the weight of the expansive film although the buoyancy ratio after immersing the sample in the buffer solution increased therewith.

Experimental Example 5

Sample and Method:

The procedure of Example 3 was followed except that the amount of the expansive film was adjusted to 6.5%, 18.0% and 24.8% on a weight basis of the cores coated with the foam layer to thereby give three test samples which were the granules of the present invention. Separately, spherical sustained release granules containing 20% of dextromethorphan hydrobromide (cf. Example 3) were employed as a control sample. Each sample was immersed in an acetate buffer solution (pH 4.0) at 37° C. and the releasing ratio of the dextromethorphan hydrobromide was determined with the lapse of time under shaking at a rate of 80 times per minute.

Result:

FIG. 6 shows the result, wherein, represents the data of the control sample, while —□—□—, —Δ—Δ— and —O—O— represent those of the test samples having expansive films in amounts of 6.5%, 18.0% and 24.8% by weight based on the cores coated with the foam layer, respectively. FIG. 6 suggests that the release of the drug can be sustained by allowing the granules to remain in the stomach. It is also found that the extent of the sustained release may be controlled by adjusting the amount of the expansive film.

EXPERIMENTAL EXAMPLE 6

The capsule according to the present invention as produced in Example 4 was administered to a beagle and granules remaining in the stomach of the animal were monitored with the lapse of time by roentgenography. As a result, it was found that all of the administered granules were in a buoyant state in the upper region of the stomach or adsorbed thereby up to one hour after the administration. It should be noted that 80 g of a liquid diet suspended in 200 ml of water was given to the animal 20 minutes before the administration.

EXPERIMENTAL EXAMPLE 7

Three capsules according to the present invention as produced in Example 5 were administered to a healthy male subject of 40 years old before breakfast and granules remaining in the stomach were monitored with the lapse of time by roentgenography. As a result, it was found that the granules were buoyant in the upper region of the stomach 30 minutes, one hour and three hours after the administration.

What is claimed is:

1. A granule of a pharmaceutical composition adapted to remain in the stomach, comprising: a core containing a pharmaceutical effective ingredient; a gas-generating layer coated on said core, said gas-generating layer comprising sodium bicarbonate and an organic acid capable of generating and evolving $CO_2$ gas when contacted by gastric juice; and an expandible film coated on and enveloping said gas-generating layer, said film being permeable to gastric juice to permit gastric juice to move therethrough into contact with said gas-generating layer and thereby to generate $CO_2$ gas inside said film, said film being impermeable to $CO_2$ gas so that said $CO_2$ gas generated in said gas-generating layer is retained inside said film and said film is expanded like a balloon by said $CO_2$ gas so that said granule becomes capable of floating on gastric juice and remains buoyant thereon for a period of time.

2. A granule as claimed in claim 1 in which said granule is capable of floating within 15 minutes after being placed on an artificial gastric juice acetate buffer solution having a pH of 4 and remain floating thereon for at least 5 hours.

3. A granule as claimed in claim 1, in which said gas-generating layer comprises an inner layer containing sodium bicarbonate and an outer layer containing an organic acid.

4. A granule as claimed in claim 1, in which said expandible film comprises a polymer which allows gastric juice to pass therethrough and expands by gas produced by the action between the gastric juice and the gas-generating layer.

5. A granule as claimed in claim 1, which comprises said core, 5 to 20 percent by weight, based on said core, of said gas-generating layer and 5 to 20 percent by weight, based on said core, of said expandible film.

6. A granule as claimed in claim 1 in which said gas-generating layer contains from 10 to 15 wt. % of sodium bicarbonate, based on the weight of said core, and the amount of said expandible film is from 7 to 15 wt. %, based on the weight of said core and said gas-generating layer.

7. A granule as claimed in claim 1 having a size of about 1 mm.

8. A capsule comprising a plurality of granules having different residence times in a stomach, said granules comprising a core containing a pharmaceutically effective ingredient; a foamable layer coated on said core in an amount of 5 to 20 percent by weight, based on said core, said foamable layer comprising an inner layer containing a bicarbonate and an outer layer containing an organic acid; and an expansive film coated on said foamable layer, said expansive film comprising a polymer which allows gastric juice to pass therethrough and expands by foam produced by the action between the gastric juice and said foamable layer, said expansive film being present in an amount of 5 to 20 percent by weight based on said core.

9. The capsule of claim 8, wherein the inner foamable layer contains sodium bicarbonate and the outer foamable layer contains an organic acid selected from the group consisting of tartaric acid, succinic acid and citric acid.

10. The capsule of claim 8, wherein the polymer of the expansive film is one or more members selected from the group consisting of polymers of polyvinyl acetate, acrylic resins, shellac, hydroxypropyl methylcellulose phthalate, cellulose acetate phthalate, methylcellulose, ethylcellulose and hydroxypropylmethylcellulose.

* * * * *